United States Patent [19]

Jenny et al.

[11] Patent Number: 5,821,374

[45] Date of Patent: Oct. 13, 1998

[54] PROCESS FOR THE OXIDATION OF ALCOHOLS

[75] Inventors: Christian-Johannes Jenny, Basel; Bruno Lohri, Kaiseraugst; Markus Schlageter, Bottmingen, all of Switzerland

[73] Assignee: Hoffmann-La Roche Inc., Nutley, N.J.

[21] Appl. No.: 747,944

[22] Filed: Nov. 12, 1996

[30] Foreign Application Priority Data

Nov. 21, 1995 [CH] Switzerland .............. 3291/95

[51] Int. Cl.$^6$ ............ C07D 305/00; C07D 319/00; C07C 45/00

[52] U.S. Cl. .......... 549/263; 549/265; 549/333; 549/476; 566/315; 566/316; 566/322; 566/361; 508/362; 508/364; 508/403; 508/407; 508/437; 508/443; 508/483; 508/486; 508/488

[58] Field of Search ............ 546/242, 184; 549/263, 265, 333, 476; 568/315, 316, 322, 361, 362, 364, 403, 407, 437, 443, 483, 486, 488

[56] References Cited

U.S. PATENT DOCUMENTS 5,416,215  5/1995  Büschken et al. ............ 546/184

FOREIGN PATENT DOCUMENTS

A-0 574 666  4/1993  European Pat. Off. .

40 07923  9/1990  Germany .

OTHER PUBLICATIONS

Derwent Abstract No. 93–406779/51.
E. G. Rozantsev, Synthesis (4):190 (1971).
P. L. Anelli, et al. J. Org. Chem., 52(12):2559–2562 (1987).
Cella et al., J. Org. Chem., vol. 40, No. 12, 1860–1862.
Derwent Abstract AN 90–298639 (for DE 40 07923).
Chemical Abstract 116:83223n.

Primary Examiner—John Kight
Assistant Examiner—Raymond Covington
Attorney, Agent, or Firm—George W. Johnston; Dennis P. Tramaloni; Bruce A. Pokras

[57] ABSTRACT

A process for oxidizing primary and secondary alcohols to the corresponding aldehydes and ketones is disclosed. The oxidation is carried out by reacting the primary or secondary alcohol with an organic N-chloro compound oxidizing agent in the presence of a catalyst of the formula:

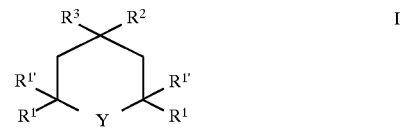

wherein the substituent groups are as defined in the specification.

29 Claims, No Drawings

PROCESS FOR THE OXIDATION OF ALCOHOLS

BACKGROUND OF THE INVENTION

The present invention is concerned with a novel process for the oxidation of primary or secondary alcohols.

Alcohols can be oxidized to aldehydes and ketones, for example, with sodium hypochlorite as the oxidizing agent and 4-methoxy-2,2,6,6-tetramethylpiperidine 1-oxide as the catalyst (*J. Org. Chem.*, Vol. 52, No. 12, 1987, pages 2559–2562). This process is not suitable for the manufacture of aldehydes and ketones which are unstable in contact with aqueous-basic media.

The object of the present invention is to provide a process for the manufacture of aldehydes and ketones which avoids aqueous-basic conditions.

SUMMARY OF THE INVENTION

The process in accordance with the invention comprises oxidizing primary or secondary alcohols by reacting them in a nonpolar, aprotic organic solvent with an organic N-chloro compound oxidizing agent in the presence of a catalyst of formula I:

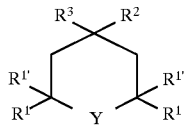

wherein $R^1$ and $R^{1'}$ are independently lower alkyl;

$R^2$ and $R^3$ are both hydrogen or are both lower alkoxy, or one is hydrogen and the other is hydroxy, lower alkoxy, lower alkylcarbonyloxy, lower alkylcarbonylamino or arylcarbonyloxy, or $R^2$ and $R^3$ together are a ketal group of formula a–c:

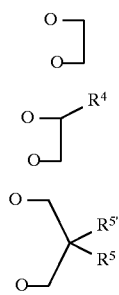

$R^4$ is lower alkyl;
$R^5$ and $R^{5'}$ are independently hydrogen or lower alkyl;
Y is a group of formula d–f:

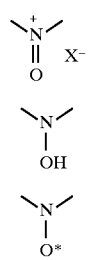

and $X^-$ is an anion.

DETAILED DESCRIPTION OF THE INVENTION

The process in accordance with the invention comprises oxidizing primary or secondary alcohols by reacting them in a nonpolar, aprotic organic solvent with an organic N-chloro compound oxidizing agent in the presence of a catalyst of formula I:

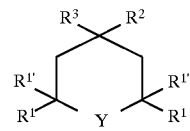

wherein $R^1$ and $R^{1'}$ are independently lower alkyl;

$R^2$ and $R^3$ are both hydrogen or are both lower alkoxy, or one is hydrogen and the other is hydroxy, lower alkoxy, lower alkylcarbonyloxy, lower alkylcarbonylamino or arylcarbonyloxy, or $R^2$ and $R^3$ together are a ketal group of formula a–c:

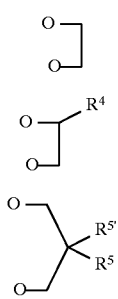

$R^4$ is lower alkyl;
$R^5$ and $R^{5'}$ are independently hydrogen or lower alkyl;
Y is a group of formula d–f:

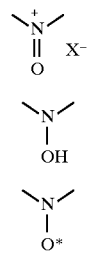

and $X^-$ is an anion.

The term "lower alkyl" means straight-chain or branched saturated hydrocarbon groups with up to 7 carbon atoms, such as methyl, ethyl, n-propyl, isopropyl, n-butyl, sec.butyl, isobutyl, n-pentyl, n-hexyl and the like.

The term "lower alkoxy" means lower alkyl groups in the sense of the foregoing definition which are bonded via an oxygen atom, such as, e.g., methoxy, butoxy and hexoxy.

The term "lower alkylcarbonyloxy" means lower alkylcarbonyl groups bonded via an oxygen atom. The term "lower alkylcarbonyl" means lower alkyl groups bonded via a carbonyl group and embraces in the sense of the foregoing definition groups such as acetyl, propionyl and the like.

The term "lower alkylcarbonylamino" means lower alkylcarbonyl groups bonded via a nitrogen atom, such as, e.g., acetylamino.

The term "arylcarbonyloxy" means arylcarbonyl groups bonded via an oxygen atom. The term "arylcarbonyl" means aryl groups bonded via a carbonyl group. The term "aryl"

means optionally substituted aromatic groups such as, for example, an optionally substituted phenyl group in which lower alkyl groups or lower alkoxy groups are the preferred substituents.

The organic N-chloro compounds useful as the source of chlorine in the process of the invention are not critical. Any conventional organic N-chloro compounds which release the N-chloro chlorine when combined with the catalyst described herein may be used in accordance with the present invention. Such N-chloro compounds may also be referred to as "chlorine-producing compounds." Preferred N-chloro compounds are N-chloro-4-toluenesulphonamide Na salt (Chloramine T), N-chloro-benzene-sulphonamide Na salt (Chloramine B), trichloroisocyanuric acid and dichlorodimethylhydantoin. Trichloroisocyanuric acid and dichlorodimethylhydantoin are especially preferred.

The process of the invention is suitable for the oxidation of primary or secondary alkyl alcohols with a straight-chain or branched hydrocarbon chain such as, e.g., 1-octanol, 2-octanol and 1-decanol; cycloalkyl alcohols such as, e.g., cyclohexanol; aliphatic alcohols which carry an aromatic substituent such as, e.g., phenylethanol, benzyl alcohol and substituted benzyl alcohols.

The process is also suitable for the oxidation of heterocyclic alcohols, especially for the oxidation of hydroxylactones such as 2-hydroxy-3,3-dimethyl-γ-butyrolactone (pantolactone) as well as of sensitive alcohols having a peroxide function such as, e.g., of (1S,4R,5R,8S)- and (1S,4S,5R,8S)-4-(hydroxymethyl)-4,8-dimethyl-2,3-dioxabicyclo[3.3.1]nonan-7-one.

The oxidation of the invention is carried out with the reactants suspended in an aprotic, nonpolar organic solvent. The sequence in which the reactants are brought together is not critical. In accordance with the invention the alcohol and the respective N-chloro compound can be suspended in an aprotic, nonpolar organic solvent and the oxidation can be initiated by adding a solution of the catalyst of formula I. However, the alcohol and the catalyst can also be suspended in an aprotic, non polar organic solvent and the oxidizing agent can be added dropwise thereto.

The molar ratio of alcohol to oxidizing agent is not critical, with lower amounts of oxidizing agent merely resulting in lower yields of the aldehyde or ketone (oxidation product) being produced. The oxidation is preferably effected using a molar ratio of alcohol to N-chloro chlorine in the oxidizing agent of about 1:1 to 1:1.25.

The addition of catalyst is essential for the oxidation in accordance with the invention. Preferred catalysts of formula I are those in which $R^1$ and $R^{1'}$ are both methyl; $R^2$ and $R^3$ are either both hydrogen or one is hydrogen and the other is acetylamino, or $R^2$ and $R^3$ together are a ketal group of formula a–c; $R^4$ is ethyl; $R^5$ and $R^{5'}$ are both methyl; Y is a group of formula f and $X^-$ is an anion. The anion is not critical, and thus may be any conventional anion that is associated with piperidine-1-oxides (compounds of formula I wherein Y is group f).

The catalysts of formula I are known compounds, with their preparation being described, for example, in European Patent Applications EPA-0 574 666 and EPA-0 574 667 or in Synthesis, 1971, p.190 et seq.

The oxidation of primary or secondary alcohols in the presence of compounds of formula I is effected with an amount of catalyst being in a range from about 0.05 mol % to about 20 mol %, with the amount being preferably in a range from about 0.1 mol % to about 1 mol %, with respect to the alcohol being oxidized.

The solvents used to suspend the reactants used in the process of the invention are not critical. Any conventional nonpolar, aprotic solvents may be used. Preferred solvents useful in accordance with the present invention are methylene chloride, ethyl acetate, acetone, chloroform, butyl acetate, diethyl ether, tert.butyl methyl ether, dichloroethane and the like. Methylene chloride, acetone and ethyl acetate are especially preferred.

The accumulation of hydrogen chloride which is liberated during the oxidation of the present invention will cause the reaction to cease before completion. Therefore, to obtain the maximum yield of oxidation product the oxidation reaction is preferably carried out in the presence of a base for the neutralization of the hydrogen chloride which is formed. The base used is not critical, so long as it is capable of neutralizing hydrogen chloride in the solvent which is used to suspend the reactants used in the process of the present invention. Examples of bases useful in accordance with the present invention are sodium acetate, sodium bicarbonate and pyridine. To obtain the maximum possible yield of oxidation product, the base should be present in an amount which is at least stoicheometrically sufficient to neutralize all the hydrogen chloride which will be liberated as a result of the process of the invention.

The temperature at which the process of the invention is carried out is not critical. The oxidation is preferably carried out at a temperature in a range from about −15° C. to about 50° C., preferably in a range from about 0° C. to about 5° C. The pressure under which the process of the invention is carried out is not critical. Preferably the oxidation is carried out under atmospheric pressure.

The following Examples illustrate the invention in more detail, but are not in any way intended to be a limitation.

The abbreviations used in the Examples for tetramethyl compounds of formula I employed are set forth hereinafter.

| Catalyst | Name |
| --- | --- |
| TEMPO (Compound A) | 2,2,6,6-Tetramethyl-1-piperidinyloxyl radical |
| TEMPO derivative B | 7,7,9,9,-Tetramethyl-1,4-dioxa-8-azaspiro[4,5]dec-8-yloxyl radical |
| TEMPO derivative C | (R,S)-2-Ethyl-7,7,9,9-tetramethyl-1,4-dioxa-8-azaspiro[4,5]dec-8-yloxyl radical |
| TEMPO derivative D | 3,3,8,8,10,10-Hexamethyl-1,5-dioxa-9-azaspiro[5,5]undec-9-yloxyl radical |
| TEMPO derivative E | 4-(Acetylamino)-2,2,6,6-tetramethyl-1-piperidinyloxyl radical |

I Oxidation of alkyl alcohols

EXAMPLE 1

Manufacture of octanal 3.5 g (15.1 mmol) of trichloroisocyanuric acid, 3.7 g (45.1 mmol) of sodium acetate and 10 mg (0.06 mmol) of TEMPO were suspended in 40 ml of methylene chloride in a 100 ml sulphonation flask and the suspension was cooled to (−7)–(−9)° C. while stirring. A solution of 5 g (38.4 mmol) of 1-octanol in 20 ml of methylene chloride was dosed in within 20 minutes, whereupon the mixture was held at (−7)–(−9)° C. for 80 minutes. Thereafter, the reaction had finished. For the working up, the white precipitate was filtered off and the filtrate was washed with sodium bicarbonate solution and with sodium chloride solution. Distillation of the crude product gave 4.5 g (91%) of octanal, GC content: (98.2%) (area percent).

EXAMPLE 2

Manufacture of 2-octanone 5 g (38.4 mmol) of 2-octanol were oxidized as described in Example 1. Distillation of the crude product gave 4.77 g (96%) of 2-octanone, GC content: (99.5%) (area percent).

EXAMPLE 3
Manufacture of decanal 6.08 g (38.4 mmol) of 1-decanol were dissolved in 58 ml of methylene chloride in a 200 ml sulphonation flask. 3.3 g (40.2 mmol) of sodium acetate and 3.6 g (15.5 mmol) of trichloroisocyanuric acid were added thereto. The mixture was cooled to 0° C. while stirring. A solution of 30 mg (0.12 mmol) of TEMPO derivative C in 3.5 ml of methylene chloride was dosed in within 30 minutes. The temperature was held at 0°–3° C. by constant cooling. The reaction had finished after 1 hour. The white precipitate was filtered off. The filtrate was worked up aqueous. 5.9 g (98%) of decanal were obtained as the crude product as a colourless liquid. GC content: 97% (area percent).

EXAMPLE 4
Manufacture of cyclohexanone 5 g (49.9 mmol) of cyclohexanol, 4.1 g (50 mmol) of sodium acetate and 10 mg (0.06 mmol) of TEMPO were suspended in 40 ml of methylene chloride in a 100 ml sulphonation flask and the suspension was cooled to (–1)–2° C. while stirring. A solution of 4.6 g (19.8 mmol) of trichloroisocyanuric acid in 20 ml of acetone was dosed in within 20 minutes, whereupon the mixture was held at (–1)–2° C. for 2.5 hours. Thereafter, the reaction had finished without any chlorination in the 2-position worth mentioning. The white precipitate was filtered off and the filtrate was washed with sodium bicarbonate solution and with sodium chloride solution. Distillation of the crude product gave 3.97 g (81%) of cyclohexanone, GC content: 98.2% cyclohexanone, 0.8% 2-chloro-cyclohexanone (area percent).

II Oxidation of aromatic alcohols

EXAMPLE 5
Manufacture of benzaldehyde
(Trichlorosocyanuric acid and TEMPO)

4.3 g (18.5 mmol) of trichloroisocyanuric acid, 3.8 g (46.2 mmol) of sodium acetate and 10 mg (0.06 mmol) of TEMPO were suspended in 40 ml of methylene chloride in a 100 ml sulphonation flask and the suspension was cooled to (–7)–(–9)° C. while stirring. A solution of 5 g (46.2 mmol) of benzyl alcohol in 20 ml of methylene chloride was dosed in within 20 minutes, whereupon the mixture was held at (–7)–(–9)° C. for 20 minutes. Thereafter, the reaction had finished. The white precipitate was filtered off and the filtrate was washed with sodium bicarbonate solution and with sodium chloride solution. Distillation of the crude product gave 4.35 g (88.6%) of benzaldehyde, GC content: (97.7%) (area percent).

EXAMPLE 6
Manufacture of benzaldehyde
(Trichloroisocyanuric acid and TEMPO derivative C)

4.15 g (38.4 mmol) of benzyl alcohol were dissolved in 58 ml of methylene chloride in a 200 ml sulphonation flask. 3.3 g (40.2 mmol) of sodium acetate and 3.6 g (15.5 mmol) of trichloroisocyanuric acid were added thereto. The mixture was cooled to 0° C. while stirring. A solution of 30 mg (0.12 mmol) of TEMPO derivative C in 3.5 ml of methylene chloride was dosed in within 30 minutes. The temperature was held at 0°–3° C. by constant cooling. The reaction had finished after 1 hour. The white precipitate was filtered off. The filtrate was worked up aqueous. 4.0 g (98%) of benzaldehyde were obtained as the crude product, GC content: 99.2%. Distillation of the crude product gave 3.22 g (79%) of benzaldehyde, GC content: 99.3% (area percent).

EXAMPLE 7
Manufacture of benzaldehyde
(1,3-Dichloro-5,5-dimethylhydantoin and TEMPO)

5.4 g (27.4 mmol) of 1,3-dichloro-5,5-dimethylhydantoin, 3.8 g (46.2 mmol) of sodium acetate and 5 g (46.2 mmol) of benzyl alcohol were suspended in 40 ml of methylene chloride in a 100 ml sulphonation flask, the suspension was cooled to 0° C. while stirring and treated with 10 mg (0.06 mmol) of TEMPO, whereupon the mixture was held at 0° C. for 80 minutes. Thereafter, the temperature was left to rise to 25° C. within 1 hour. The mixture was stirred at 25° C. for a further 16 hours. Thereafter, the reaction had finished. The white precipitate was filtered off and the filtrate was washed with sodium bicarbonate solution and with sodium chloride solution. Distillation of the crude product gave 4.0 g (81.5%) of benzaldehyde, GC content: (99.7%) (area percent).

EXAMPLE 8
Manufacture of 4-nitrobenzaldehyde 5 g (32.6 mmol) of 4-nitrobenzylalcohol, 2.7 g (32.9 mmol) of sodium acetate and 10 mg (0.06 mmol) of TEMPO were suspended in 40 ml of methylene chloride in a 100 ml sulphonation flask and the suspension was cooled to (–8)–(–10)° C. while stirring. A solution of 3.03 g (13.0 mmol) of trichloroisocyanuric acid in 20 ml of acetone was dosed in within 1 hour, whereupon the mixture was held at (–5)° C. for 1 hour. Thereafter, the reaction had finished. The white precipitate was filtered off and the filtrate was washed with sodium bicarbonate solution and with sodium chloride solution. The organic phase was concentrated and the residue was recrystallized from diisopropyl ether. There were obtained 4.62 g (94%) of 4-nitrobenzaldehyde, GC content: (97.7%) (area percent).

EXAMPLE 9
Manufacture of acetophenone 4.7 g (38.4 mmol) of rac.-1-phenylethanol and 3.18 g (40.2 mmol) of pyridine were dissolved in 60 ml of ethyl acetate under an inert gas in a 200 ml sulphonation flask. The mixture was cooled to 0° C. while stirring and treated with 60 mg (0.28 mmol) of TEMPO derivative E. Thereafter, a solution of 3.6 g (15.5 mmol) of trichloroisocyanuric acid in 38 ml of ethyl acetate was dosed in within 1 hour at a temperature of 0°–3° C. The reaction mixture was stirred at 0°–3° C. for a further 1 hour. Thereafter, the reaction had finished. The white precipitate was filtered off and the filtrate was treated with a solution of sodium pyrosulphite in order to reduce the excess trichloroisocyanuric acid. The filtrate was washed with sodium bicarbonate solution and with sodium chloride solution. 4.7 g (102%) of acetophenone were obtained as the crude product, GC content: 99.8%. Distillation of the crude product gave 3.19 g (69%) of acetophenone, GC content: 99.9% (area percent).

EXAMPLE 10
Manufacture of anisaldehyde
(Trichloroisocyanuric acid)

5 g (36.2 mmol) of 4-anisyl alcohol, 3.0 g (36.6 mmol) of sodium acetate and 10 mg (0.06 mmol) of TEMPO were suspended in 40 ml of methylene chloride in a 100 ml sulphonation flask and the suspension was cooled to (–8)–(–10)° C. while stirring. A solution of 3.4 g (14.5 mmol) of trichloroisocyanuric acid in 20 ml of acetone was dosed in within 40 minutes, whereupon the mixture was held at 0° C. for 1 hour. Thereafter, the reaction had finished. The white precipitate was filtered off and the filtrate was washed with sodium bicarbonate solution and with sodium chloride solution. The organic phase was concentrated. 5.2g of crude product in the form of a mixture comprising anisaldehyde and 4-chloroanisole were obtained. GC content: 46.7% 4-chloroanisole, 20.7% anisaldehyde (area percent).

EXAMPLE 11
Manufacture of anisaldehyde
(1,3-Dichloro-5,5-dimethylhydantoin)

5 g (36.2 mmol) of anisyl alcohol, 3.0 g (36.6 mmol) of sodium acetate and 4.2 g (21.3 mmol) of dichlorodimethylhydantoin were suspended in 40 ml of methylene chloride in a 100 ml sulphonation flask. The suspension was cooled to 0° C. while stirring and treated with 10 mg (0.06 mmol) of TEMPO, whereupon the mixture was held at 0° C. for 16 hours. Thereafter, the reaction had finished without 4-chloro-anisole being formed in any amount worth mentioning. The white precipitate was filtered off and the filtrate was washed with sodium bicarbonate solution and with sodium chloride solution. Distillation of the crude product gave 4.49 g (91%) of anisaldehyde GC content: 88.8% (area percent).

EXAMPLE 12
Manufacture of dihydro-4,4-dimethyl-2,3-furandione (ketopantolacetone)
(TEMPO)

5 g (38.4 mmol) of 2-hydroxy-3,3-dimethyl-γ-butyrolactone (pantolactone) were dissolved in 118 ml of methylene chloride in a 200 ml sulphonation flask. 3.3 g (40.2 mmol) of sodium acetate and 3.6 g (15.5 mmol) of trichloroisocyanuric acid were added thereto. The mixture was cooled to 0° C. while stirring. A solution of 38.2 mg (0.24 mmol) of TEMPO in 2 ml of methylene chloride was dosed in within 10 minutes. The temperature was held at 0°–3° C. by constant cooling. After a reaction period of 7 hours the white precipitate was filtered off. The filtrate was concentrated. Chromatography of the residue (SiO$_2$, toluene/ethyl acetate 85:15) and subsequent recrystallization of the chromatographed product gave 4.23g (86%) of ketopantolactone, m.p. 67.5°–68° C., GC content: 100% (area percent).

EXAMPLE 13
Manufacture of dihydro-4,4-dimethyl-2,3-furandione (ketopantolacetone)
(TEMPO derivative B)

5 g (38.4 mmol) of 2-hydroxy-3,3-dimethyl-γ-butyrolactone (pantolactone) were dissolved in 118 ml of methylene chloride in a 200 ml sulphonation flask. 3.3 g (40.2 mmol) of sodium acetate and 3.6 g (15.5 mmol) of trichloroisocyanuric acid were added thereto. The mixture was cooled to 0° C. while stirring. A solution of 60 mg (0.28 mmol) of TEMPO derative B in 2 ml of methylene chloride was dosed in within 10 minutes. The temperature was held at 0°–3° C. by constant cooling. The reaction had finished after 3 hours. The white precipitate was filtered off and the filtrate was treated with sodium bisulphite solution in order to reduce the excess trichloroisocyanuric acid. Working up of the reaction mixture and subsequent recrystallization of the crude product gave 3.5 g (71%) of ketopantolactone, GC content: 99.6% (area percent).

EXAMPLE 14
Manufacture of dihydro-4,4-dimethyl-2,3-furandione (ketopantolacetone)
(TEMPO derivative C)

5 g (38.4 mmol) of pantolactone were reacted with 3.6 g (15.5 mmol) of trichloroisocyanuric acid as described in Example 13. In contrast to Example 13, 60 mg (0.25 mmol) of TEMPO derivative C were used as the catalyst. The reaction had finished after 3 hours. After recrystallization of the crude product there were obtained 4.6 g (93%) of ketopantolactone, m.p. 69°–70° C., GC content: 100% (area percent).

EXAMPLE 15
Manufacture of dihydro-4,4-dimethyl-2,3-furandione (ketopantolacetone)
(TEMPO derivative D)

5 g (38.4 mmol) of pantolactone were reacted with 3.6 g (15.5 mmol) of trichloroisocyanuric acid as described in Example 13. In contrast to Example 13, 63 mg (0.24 mmol) of Tempo derivative D were used as the catalyst. The reaction had finished after 1 hour. After recrystallization of the crude product there were obtained 4.85 g (98%) of ketopantolactone, m.p. 68°–69° C., GC content: 100% (area percent).

EXAMPLE 16
Manufacture of dihydro-4,4-dimethyl-2,3-furandione (ketopantolacetone)
(TEMPO derivative C, ethyl acetate as the solvent)

2.5 g (19.2 mmol) of pantolactone were reacted with 1.8 g (7.7 mmol) of trichloroisocyanuric acid in the presence of 30 mg (0.12 mmol) of TEMPO derivative C and 1.65g (20.1 mmol) of sodium acetate analogously to Example 14. In contrast to Example 14, ethyl acetate (20 ml) was used as the solvent. The reaction had finished after 2 hours. After recrystallization of the crude product there were obtained 2.2 g (89%) of ketopantolactone, m.p. 68°–69° C., GC content: 100% (area percent).

III Oxidation of a mixture of peroxo alcohols

EXAMPLE 17
Manufacture of (1S,4R,5R,8S)-4,8-dimethyl-7-oxo-2,3-dioxa-bicyclo[3.3.1]nonane-4-carboxaldehyde and (1S,4S,5R,8S)-4,8-dimethyl-7-oxo-2,3-dioxabicyclo[3.3.1]nonane-4-carboxaldehyde 183.8 g of alcohol mixture (HPLC content 46.2% (1S,4R,5R,8S)-4-(hydroxymethyl)-4,8-dimethyl-2,3-dioxabicyclo[3.3.1]nonan-7-one+47.5% (1S,4S,5R,8S)-4-(hydroxymethyl)-4,8-dimethyl-2,3-dioxabicyclo[3.3.1]nonan-7-one, max. 919 mmol), 77.7 g (940 mmol) of sodium acetate and 84.7 g (346 mmol) of trichloroisocyanuric acid were suspended in 2700 ml of methylene chloride in a 4500 ml sulphonation flask, the suspension was cooled to 0° while stirring and treated within 5 minutes with a solution of 368 mg (2.35 mmol) of TEMPO in 10 ml of methylene chloride. The mixture was held at 0°–3° C. for 5 hours. Thereafter, the reaction had finished. The white precipitate was filtered off and the filtrate was washed with sodium sulphate solution. Crude product comprising 169.3 g (>90%) of a 1:1 mixture of the aldehydes was obtained as a solid yellowish mass (HPLC content: 42.3% (1S,4R,5R,8S)-4,8-dimethyl-7-oxo-2,3-dioxabicyclo[3.3.1]nonane-4-carboxaldehyde, 45.8% (1S,4S,5R,8S)-4,8-dimethyl-7-oxo-2,3-dioxabicyclo[3.3.1]nonane-4-carboxaldehyde).

EXAMPLE 18
(Comparative Example)
Manufacture of dihydro-4,4-dimethyl-2,3-furandione (ketopantolacetone)
without TEMPO catalyst 1.18 g (9.1 mmol) of pantolactone were dissolved in 27 ml of methylene chloride at 22° C. in a 50 ml reaction flask. 777 mg (9.5 mmol) of sodium acetate and 850 mg (3.7 mmol) of trichloroisocyanuric acid were added thereto. The mixture was cooled to 0° C. while stirring. 18.5% of ketopantolactone were obtained after a reaction period of 6 hours at 0° C. After a further reaction period of 20 hours at 22° C. the composition was 22.2% of ketopantolactone and 77.5% of pantolactone (area percent).

We claim:

1. A process for oxidizing a primary or secondary alcohol to the corresponding aldehyde or ketone which process comprises reacting in a nonpolar, aprotic solvent the primary or secondary alcohol with an organic N-chloro compound oxidizing agent in the presence of a catalyst of the formula:

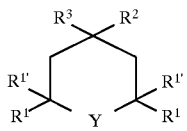

wherein $R^1$ and $R^{1'}$ are independently lower alkyl;

$R^2$ and $R^3$ are both hydrogen or are both lower alkoxy, or one is hydrogen and the other is hydroxy, lower alkoxy, lower alkylcarbonyloxy, lower alkylcarbonylamino or arylcarbonyloxy, or $R^2$ and $R^3$ together are a ketal group of the formula:

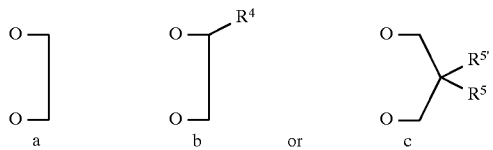

$R^4$ is lower alkyl;
$R^5$ and $R^{5'}$ are independently hydrogen or lower alkyl;
Y is a group of the formula:

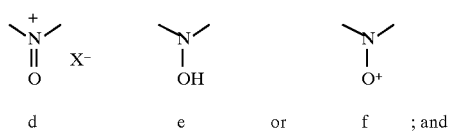

$X^-$ is an anion;

so that the primary or secondary alcohol is oxidized to the corresponding aldehyde or ketone.

2. The process of claim 1 wherein $R^1$ and $R^{1'}$ are both methyl; $R^2$ and $R^3$ are both hydrogen, or one of $R^2$ and $R^3$ is hydrogen and the other is acetylamino, or $R^2$ and $R^3$ together are a ketal group of formula a–c; $R^4$ is ethyl; $R^5$ and $R^{5'}$ are both methyl; and Y is a group of formula f.

3. The process of claim 2 wherein the catalyst is present in an amount in the range from about 0.05 mol % to about 20 mol % of the amount of the alcohol.

4. The process of claim 3 wherein the oxidizing agent is N-chloro-4-toluenesulphonamide Na salt, N-chlorobenzene-sulphonamide Na salt, trichloroisocyanuric acid or dichlorodimethylhydantoin.

5. The process of claim 4 wherein the oxidizing agent is trichloroisocyanuric acid or dichlorodimethylhydantoin.

6. The process of claim 5 wherein the molar ratio of the alcohol to the N-chloro chlorine in the oxidizing agent is in a range from about 1:1 to about 1:1.25.

7. The process of claim 6 wherein the catalyst is present in an amount in a range from about 0.1 mol % to about 1 mol % of the amount of the alcohol.

8. The process of claim 7 wherein the oxidation is carried out at a temperature in a range from about −15° C. to about 50° C.

9. The process of claim 8 wherein the oxidation is carried out at a temperature in a range from about 0° C. to about 5° C.

10. A process for oxidizing a hydroxylactone to the corresponding ketone which process comprises reacting in a nonpolar, aprotic solvent the hydroxylactone with an organic N-chloro compound oxidizing agent in the presence of a catalyst of the formula:

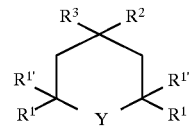

wherein $R^1$ and $R^{1'}$ are independently lower alkyl;

$R^2$ and $R^3$ are both hydrogen or are both lower alkoxy, or one is hydrogen and the other is hydroxy, lower alkoxy, lower alkylcarbonyloxy, lower alkylcarbonylamino or arylcarbonyloxy, or $R^2$ and $R^3$ together are a ketal group of the formula:

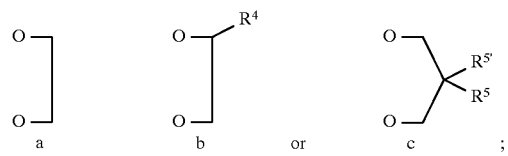

$R^4$ is lower alkyl;
$R^5$ and $R^{5'}$ are independently hydrogen or lower alkyl;
Y is a group of the formula:

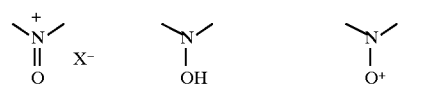

$X^-$ is an anion;

so that the hydroxylactone is oxidized to the corresponding ketone.

11. The process of claim 10 wherein $R^1$ and $R^{1'}$ are both methyl; $R^2$ and $R^3$ are both hydrogen, or one of $R^2$ and $R^3$ is hydrogen and the other is acetylamino, or $R^2$ and $R^3$ together are a ketal group of formula a–c; $R^4$ is ethyl; $R^5$ and $R^{5'}$ are both methyl; and Y is a group of formula f.

12. The process of claim 11 wherein the catalyst is present in an amount in the range from about 0.05 mol % to about 20 mol % of the amount of the alcohol.

13. The process of claim 12 wherein the hydroxylactone is pantolactone and the ketone is ketopantolacetone.

14. The process of claim 13 wherein the oxidizing agent is N-chloro-4-toluenesulphonamide Na salt, N-chlorobenzene-sulphonamide Na salt, trichloroisocyanuric acid or dichlorodimethylhydantoin.

15. The process of claim 14 wherein the oxidizing agent is trichloroisocyanuric acid or dichlorodimethylhydantoin.

16. The process of claim 15 wherein the molar ratio of the alcohol to the N-chloro chlorine in the oxidizing agent is in a range from about 1:1 to about 1:1.25.

17. The process of claim 16 wherein the catalyst is present in an amount in a range from about 0.1 mol % to about 1 mol % of the amount of the alcohol.

18. The process of claim 17 wherein the oxidation is carried out at a temperature in a range from about −15° C. to about 50° C.

19. The process of claim 18 wherein the oxidation is carried out at a temperature in a range from about 0° C. to about 5° C.

20. A process for oxidizing a peroxo alcohol to the corresponding aldehyde which process comprises reacting in a nonpolar, aprotic solvent the peroxo alcohol with an organic N-chloro compound oxidizing agent in the presence of a catalyst of the formula:

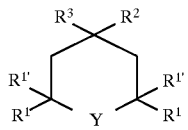  I wherein $R^1$ and $R^{1'}$ are independently lower alkyl;

$R^2$ and $R^3$ are both hydrogen or are both lower alkoxy, or one is hydrogen and the other is hydroxy, lower alkoxy, lower alkylcarbonyloxy, lower alkylcarbonylamino or arylcarbonyloxy, or $R^2$ and $R^3$ together are a ketal group of the formula:

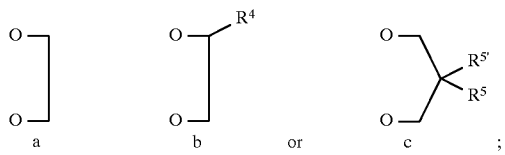

$R^4$ is lower alkyl;

$R^5$ and $R^{5'}$ are independently hydrogen or lower alkyl;

Y is a group of the formula:

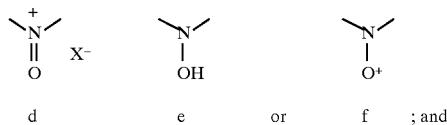

$X^-$ is an anion;

so that the peroxo alcohol is oxidized to the corresponding aldehyde.

21. The process of claim 20 wherein $R^1$ and $R^{1'}$ are both methyl; $R^2$ and $R^3$ are both hydrogen, or one of $R^2$ and $R^3$ is hydrogen and the other is acetylamino, or $R^2$ and $R^3$ together are a ketal group of formula a–c; $R^4$ is ethyl; $R^5$ and $R^{5'}$ are both methyl; and Y is a group of formula f.

22. The process of claim 21 wherein the catalyst is present in an amount in the range from about 0.05 mol % to about 20 mol % of the amount of the alcohol.

23. The process of claim 22 wherein the peroxo alcohol is (1S,4R,5R,8S)-4-(hydroxymethyl)-4,8-dimethyl-2,3-dioxabicyclo[3.3.1]nonan-7-one and the aldehyde is (1S,4R,5R,8S)-4,8-dimethyl-7-oxo-2,3-dioxabicyclo[3.3.1]nonane-4-carboxaldehyde, or the peroxo alcohol is (1S,4S,5R,8S)-4-(hydroxymethyl)-4,8-dimethyl-2,3-dioxabicyclo[3.3.1]nonan-7-one and the aldehyde is (1S,4S,5R,8S)-4,8-dimethyl-7-oxo-2,3-dioxabicyclo[3.3.1]nonane-4-carboxaldehyde.

24. The process of claim 23 wherein the oxidizing agent is N-chloro-4-toluenesulphonamide Na salt, N-chloro-benzene-sulphonamide Na salt, trichloroisocyanuric acid or dichlorodimethylhydantoin.

25. The process of claim 24 wherein the oxidizing agent is trichloroisocyanuric acid or dichlorodimethylhydantoin.

26. The process of claim 25 wherein the molar ratio of the alcohol to the active chlorine in the oxidizing agent is in a range from about 1:1 to about 1:1.25.

27. The process of claim 26 wherein the catalyst is present in an amount in a range from about 0.1 mol % to about 1 mol % of the amount of the alcohol.

28. The process of claim 27 wherein the oxidation is carried out at a temperature in a range from about −15° C. to about 50° C.

29. The process of claim 28 wherein the oxidation is carried out at a temperature in a range from about 0° C. to about 5° C.

* * * * *